United States Patent
Perrett et al.

(10) Patent No.: US 9,664,686 B2
(45) Date of Patent: May 30, 2017

(54) IMAGING SYSTEM AND ASSOCIATED METHOD FOR DETECTION OF PROTEIN CONTAMINATION

(75) Inventors: David Perrett, London (GB); Nanda Kishore Nayuni, London (GB); Paul Ellwood, Cambridge (GB); Richard Maskell, Saffron Walden (GB); Alasdair Hayden Wright, Cambridge (GB); Sarah Thompson, Ely (GB); Laura Sullivan, Cambridgeshire (GB)

(73) Assignee: Synoptics Limited, Cambridge (GB)

( * ) Notice: Subject to any disclaimer, the term of this patent is extended or adjusted under 35 U.S.C. 154(b) by 0 days.

(21) Appl. No.: 13/817,911

(22) PCT Filed: Aug. 12, 2011

(86) PCT No.: PCT/GB2011/051534
§ 371 (c)(1),
(2), (4) Date: May 15, 2013

(87) PCT Pub. No.: WO2012/022963
PCT Pub. Date: Feb. 23, 2012

(65) Prior Publication Data
US 2013/0224869 A1    Aug. 29, 2013

(51) Int. Cl.
*G01N 33/68* (2006.01)
*G01N 21/64* (2006.01)
(Continued)

(52) U.S. Cl.
CPC ..... *G01N 33/6839* (2013.01); *G01N 21/6428* (2013.01); *G01N 21/6456* (2013.01); *G01N 21/94* (2013.01)

(58) Field of Classification Search
CPC ........... G01N 21/6428; G01N 33/6839; G01N 21/94; G01N 21/6456
(Continued)

(56) References Cited

U.S. PATENT DOCUMENTS 6,653,146 B1 *  11/2003  Ruvinsky et al. ............ 436/172
7,547,552 B2 *  6/2009   Doi et al. ..................... 436/15
(Continued)

FOREIGN PATENT DOCUMENTS

DE   20 2008 012267    2/2009
EP        1347285 A1    9/2003
(Continued)

OTHER PUBLICATIONS

International Search Report and Written Opinion of corresponding International Application No. PCT/GB2011/051534, dated Nov. 15, 2011.
(Continued)

*Primary Examiner* — Rebecca M Fritchman
(74) *Attorney, Agent, or Firm* — Renner, Otto, Boisselle and Sklar LLP

(57) ABSTRACT

An imaging system (10) and associated method for detection of protein contamination on a surgical instrument (100) that has been treated with a fluorescing stain, wherein fluorophors in the stain are capable of emitting light of an emitted type when both excited by light of an excitation type and in contact with a protein are provided. The system comprises a light tight chamber (14) for receiving the instrument (100). Inside the chamber (14) are both visible light sources (20) and excitation light sources (22) for respectively illuminating the chamber with visible and excitation type light. A digital camera (30) is able to capture a first image of the instrument (100) as illuminated by the visible light, and a second image, of patterns of fluorescence produced by the fluorophors in the stain corresponding to protein contamination. The first and second images are combined to produce a composite image of the instrument (100) highlighting the areas of protein contamination. Associated software can be
(Continued)

used to analyse the images so as to determine a level of protein contamination.

15 Claims, 2 Drawing Sheets

(51) Int. Cl.
*G01N 33/00* (2006.01)
*G01N 21/94* (2006.01)

(58) Field of Classification Search
USPC .......................................... 422/82.08; 436/86
See application file for complete search history.

(56) References Cited

U.S. PATENT DOCUMENTS

| | | |
|---|---|---|
| 2002/0154798 A1* | 10/2002 | Cong .................... G01N 15/14 |
| | | 382/128 |
| 2003/0173525 A1 | 9/2003 | Seville |
| 2004/0066979 A1* | 4/2004 | Gindele et al. ............... 382/274 |
| 2006/0008866 A1 | 1/2006 | Flick et al. |
| 2006/0024209 A1* | 2/2006 | Agnew ......................... 422/100 |

FOREIGN PATENT DOCUMENTS

| | | |
|---|---|---|
| EP | 1 376 102 | 1/2004 |
| WO | 02/051451 | 7/2002 |
| WO | 2004025295 A2 | 3/2004 |

OTHER PUBLICATIONS

Office Action on corresponding Chinese Application CN201180047673.7 dated Aug. 29, 2014.

\* cited by examiner

IMAGING SYSTEM AND ASSOCIATED METHOD FOR DETECTION OF PROTEIN CONTAMINATION

FIELD OF THE INVENTION

The invention relates to an apparatus for measuring protein contamination, specifically on surgical instruments, and to associated methods. In particular, the invention relates to an instrument that is designed to be used in conjunction with a stain comprising a reagent composition that fluoresces in the presence of protein matter (such as intact proteins and/or their subunit amino acids and peptides), such as the compositions described in the co-pending application entitled "IN-SITU REAGENT", filed on the same date under attorney reference KS.P49074GB.

BACKGROUND TO THE INVENTION

In view of increased concerns relating to the role of proteins in the transmission of diseases, healthcare authorities might impose mandatory protein contamination detection requirements on the use of all surgical instruments.

Currently, detection of protein residues on surgical instruments is carried out using a standard Ninhydrin assay. However, this standard assay has been shown to be unreliable, because it is ineffective in detecting all but two amino acids which are water soluble and which would in any event rarely present a problem. Moreover, the Ninhydrin test is often carried out by 'swabbing' instruments and testing the swab. It is difficult to swab all portions of an instrument, particularly in areas that are most prone to collect protein residues, such as corners and recesses.

A further consideration is cost. Currently, a pack of four Ninhydrin tests with positive controls costs £25. The test is also relatively time-consuming to carry out and requires trained personnel.

The present invention aims to address these issues and to provide a quick, accurate method for detecting protein contamination over an entire instrument. The inventive detection method is many times more sensitive than the Ninhydrin technique.

A stain comprising a reagent composition has been developed that fluoresces in the presence of protein. Fluorophors in the stain are capable of emitting light of an emitted type when and only when both excited by light of an excitation type and in contact with a protein. Details of the stain are disclosed in co-pending application entitled "REAGENT", filed on the same date under attorney reference KS.P49074GB. The components of the stain are readily available and inexpensive.

SUMMARY OF THE INVENTION

According to a first aspect of the invention, there is provided an imaging system for detection of protein contamination on a specimen that has been treated with a fluorescing stain, wherein fluorophors in the stain are capable of emitting light of an emitted type when both excited by light of an excitation type and in contact with a protein, the system comprising:
  a chamber for receiving the specimen;
  a first light source adapted to illuminate the specimen with light of the excitation type when, in use, the specimen is received in the chamber;
  a first image capture device adapted to capture a second image, of patterns of fluorescence emitted by the fluorophors in the stain on the specimen, corresponding to protein contamination, when illuminated by the second light source; and
  means for indicating, dependent on said first image capture, whether the specimen is contaminated with protein.

The imaging system is able to provide a quick, accurate determination of whether a specimen is contaminated with protein.

The system may further comprise means for determining the level of protein contamination. By determining the level of protein contamination, it is possible to make a more informed decision as to whether the specimen is contaminated to such an extent that it must be unfit for use. Moreover, healthcare authorities might set standard acceptable threshold levels, whereby if contamination levels are determined to be above a particular threshold the specimen must be sterilised or scrapped. The means for determining the level of protein contamination may comprise a processor and associated analysis software.

The system may further comprise means to detect extraneous signals and means to compensate for any such signals.

The system may further comprise a filter between the specimen and the first image capture device, the filter adapted to transmit light of said emitted type and to prevent transmission of light of said excitation type. The filter is preferably adapted to transmit only light having a wavelength in the range of 430 nm to 450 nm.

The light of the excitation type may typically be in the range of 270 nm to 370 nm. Preferably, the light of the excitation type has a 312 nm peak wavelength.

The specimen may typically comprise a surgical instrument. The invention has particular implementation in the context of surgical instruments, due to the critical need for these to be verified as sterile prior to use. Should the system indicate that the instrument is contaminated, the instrument could be sent to be sterilised or discarded.

The system may further comprise:
  a second light source adapted to illuminate the specimen with visible light when, in use, the specimen is received in the chamber; and
  a second image capture device adapted to capture a second image, of the specimen, when illuminated by the second light source. The system may yet further comprise an image combiner adapted to combine the first and second images. The addition of a visible image of the specimen, particularly when combined with the fluorescing image, offers several advantages. Firstly, the combined captured images may be displayed to provide a clear visual indication to a user as to whether protein contamination is present. Secondly, as explained below, the visible image of the specimen may be used as a mask so as to ignore any (extraneous) signals than might occur in the fluorescing image outside of the area of the specimen.

Preferably, the first image capture device comprises a digital camera.

Preferably, the second image capture device comprises a digital camera. A single digital camera may function as both the first image capture device and the second image capture device. A single piece of equipment adapted to carry out dual functions might be the most cost-effective solution. However, it can be seen that by having separate, more specialised equipment for each distinct image capture task more accurate results might be achieved.

Where the system further comprises means for determining the level of protein contamination, said means for indicating may comprise an indicator adapted to indicate whether the level of protein contamination is below or above a predetermined threshold, thus providing a simple pass/fail indication. Such an indicator would provide a simple, clear way to identify whether the specimen has passed or failed the contamination test. Optionally, the indicator might further be adapted to indicate whether the level of protein contamination is close to the predetermined threshold, which might require the test to be re-run. Such an indicator might, for example comprise a 'traffic light' system having a red light for a 'fail', a green light for a 'pass' and an amber light for 'further attention'.

Preferably, the stain comprises a protein and/or amino acid detecting composition comprising:
(a) o-phthaldialdehyde,
(b) a $C_3$-$C_6$ thiol,
(c) a buffer in the range of pH from 7.5 to 10, and
(d) a surfactant,
wherein the composition further comprises (e) a thiol reducing compound.

Further preferably, the composition is prepared by combining:
(a) about 0.1 mmol/L to about 10 mmol/L of o-phthaldialdehyde,
(b) 1 mM to 20 mM of a $C_3$-$C_6$ thiol,
(c) 10 mM to 100 mM of a buffer in the pH range from 7.5 to 10,
(d) 0.01% v/v to 2% v/v of a surfactant, and
(e) about 0.05 mmol/L to about 5 mmol/L of the thiol reducing compound.

According to a second aspect of the invention, there is provided a method of detecting protein contamination on a specimen, the method comprising the steps of:
treating the specimen with a fluorescing stain, wherein fluorophors in the stain are capable of emitting light of an emitted type when both excited by light of an excitation type and in contact with a protein;
placing the treated specimen within a chamber;
illuminating the specimen with light of the excitation type, and, when so illuminated, capturing a first image, of patterns of fluorescence emitted by the fluorophors in the stain on the specimen, corresponding to protein contamination; and
dependent on said first image capture, indicating whether the specimen is contaminated with protein.

The method may further comprise a step of determining the level of protein contamination.

The method may further comprise the step of illuminating the specimen with visible light, and, when so illuminated, capturing a second image of the specimen. The method may even further comprise the step of combining the first and second images. As noted above, the addition of a visible image of the specimen, particularly when combined with the fluorescing image, offers several advantages.

The method may further comprise the steps of:
detecting extraneous signals; and
compensating for any such extraneous signals;
wherein the detecting step comprises measuring a background signal level, and wherein the compensating step comprises subtracting the background signal level from the first image. In one embodiment, said measuring comprises summing the grey level values in the first image. In another embodiment, said measuring comprises low pass filtering the first image. In yet another embodiment, said measuring comprises measuring the minimum signal level in the first image, and said compensating comprises subtracting said minimum signal level from every point in the second image. In a different embodiment, said measuring comprises the steps of:
illuminating the chamber with light of the excitation type, with no specimen present in the chamber; and
when so illuminated, capturing a background image of the chamber;
and wherein said compensating comprises subtracting said background image from the first image on a pixel by pixel basis.

Where the method further comprises the step of illuminating the specimen with visible light, and, when so illuminated, capturing a second image of the specimen, that second image may be used in a masking step in which all signals emanating from an area of the first image outside of the specimen, as captured in the second image, are rejected. 'Foreign matter', such as bits of tissue or dust or other debris can fluoresce. One way to eliminate extraneous signals due to such foreign matter within the chamber is to identify the shape of the contaminated specimen from the visible image and then to limit the measurements to within that shape. Thus, any signals from outside the detected specimen shape can be rejected as "not from contamination on the specimen".

The method may further comprise a calibration step comprising carrying out the steps on a specimen having a known standard amount of protein.

BRIEF DESCRIPTION OF THE DRAWINGS

The invention will be described, by way of example, with reference to the accompanying drawings, in which.

DETAILED DESCRIPTION

Figure 1:
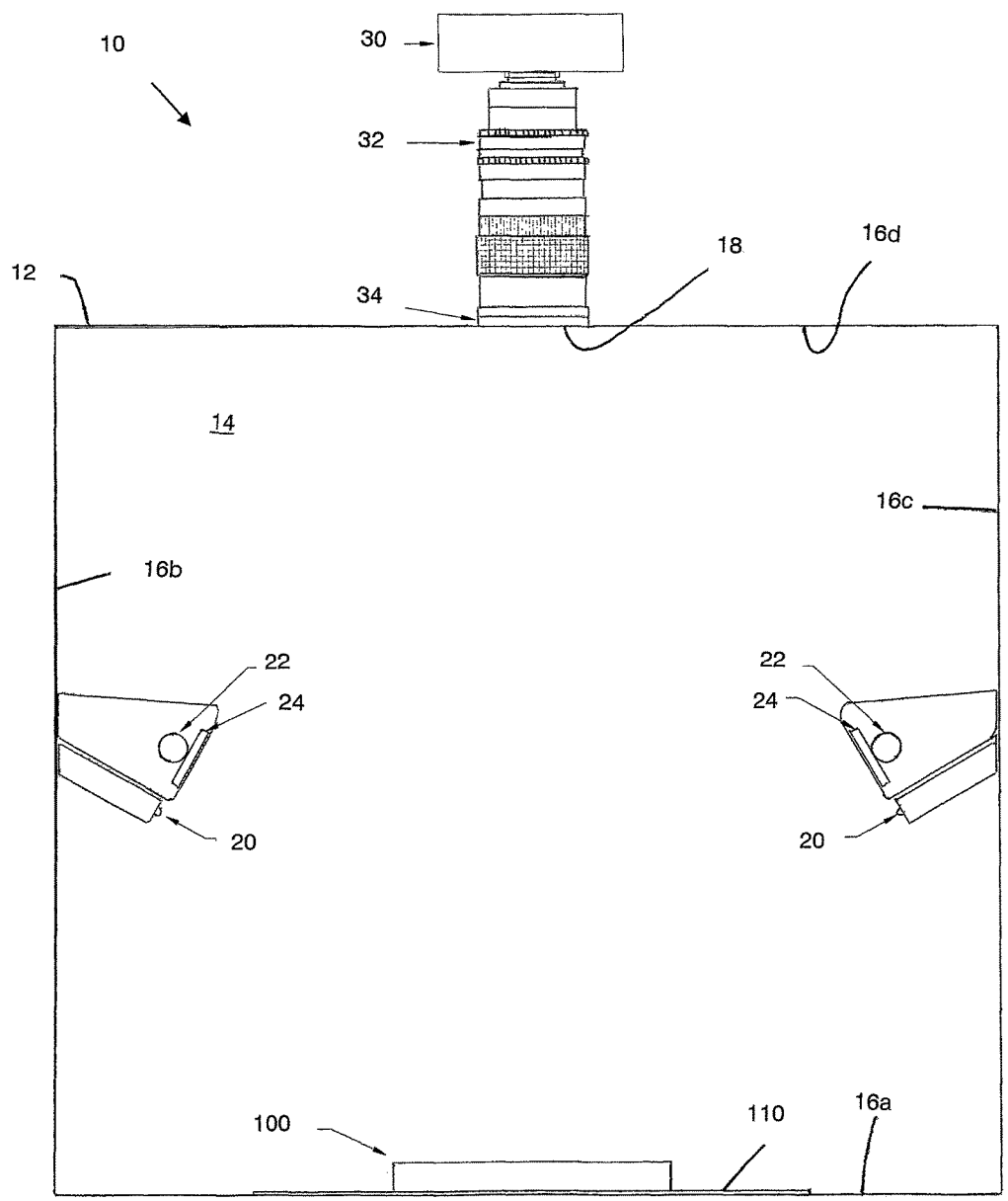
FIG. 1 is a schematic representation of the system of the invention, showing the interior of the chamber in cross section.

FIG. 1 shows, schematically, an imaging system 10 for detection of protein contamination on a specimen 100. Preferably, the specimen 100 is a surgical instrument. The system and associated method rely on a stain that fluoresces in the presence of protein, as discussed in the 'Background to the Invention'.

The specimen 100 is coated with the stain, such as by dipping or spraying.

The system comprises a housing 12, such as a cabinet, the interior of which defines a chamber 14. The chamber 14 is impervious to light, so providing a totally dark imaging space. The internal walls 16 of the chamber 14 are treated with non-reflective material to enhance the darkness and improve system performance. One example of a suitable treatment is to paint the walls 16 with matt black paint. Another suitable treatment is to line the interior walls 16 with matt black anodised aluminium foil.

The interior of the cabinet 12 is accessible via an access opening such as a door or a drawer (not shown). The edges of the access opening are adapted to prevent ambient light from entering the chamber 14, for example including flexible seals and/or light tight labyrinths. The specimen 100 can be placed through the door or into the drawer for location inside the chamber 14 for imaging. The specimen 100 may rest on a tray 110, the tray and specimen together being placed on a bottom wall 16a of the chamber 14. Alternatively, the specimen 100 may be placed directly on the bottom wall 16c.

Where the system includes a drawer, the specimen might be sprayed with the stain after having been placed in the drawer.

Light sources are located on opposite side walls 16b, 16c on the inside of the chamber 14. Visible light sources 20 are located and oriented to evenly illuminate the specimen 100. The visible light sources 20 emit broad spectrum light in the range of 380-750 nm. In this embodiment, excitation light sources 22 are located directly above the respective visible light sources 20 and are capable of exciting the stain on the coated specimen 100. However, alternative lighting positions are possible.

The excitation light sources 22 emit light in the range of 270 nm to 370 nm, which is optimal for excitation of the stain. Optionally, an excitation filter 24 is associated with each respective excitation light source 22 so that the excitation light sources 22 do not emit light within the emission spectra of the stain. In one embodiment, the excitation light sources 22 emit mid wave or long wave ultra violet light that is filtered.

The top wall 16d of the housing 12 includes an aperture 18. A digital camera 30 and lens 32 are located on the exterior of the top wall 16d, outside the chamber 14 and aligned with the aperture 18. The specimen 100 is included in the camera's field of view. An emission filter 34 is located between the specimen 100 and the camera 30. The emission filter 34 is adapted to transmit light of said emitted type and to prevent transmission of light of said excitation type, thereby to improve the sensitivity of the system by rejecting any signal other than that emitted by the stain, such as leakage from the excitation lights 22.

Figure 3:
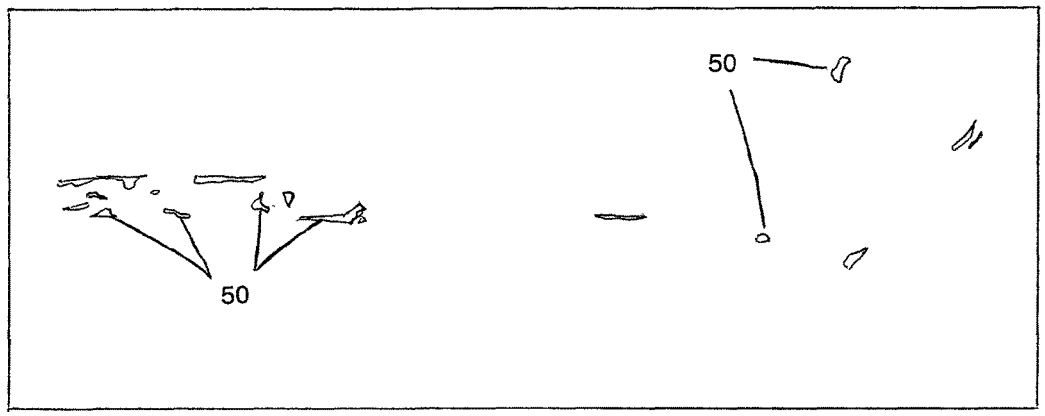
FIG. 3 is an illustration of the same instrument, corresponding to the first image of the invention, in which protein contamination patches are visible.

In use, a user coats the surgical instrument 100 to be inspected with the stain and places it inside the chamber 14, closing the drawer or door to make the chamber 14 light tight. The excitation light sources 22 are turned on to illuminate the instrument. Whilst so illuminated, the camera 30 captures a first image of patterns of fluorescence 50 emitted by the stain where in contact with protein on the instrument 100 (see FIG. 3). As an example, with a mid wave UV excitation light source, 4 s is an appropriate exposure time.

Figure 2:
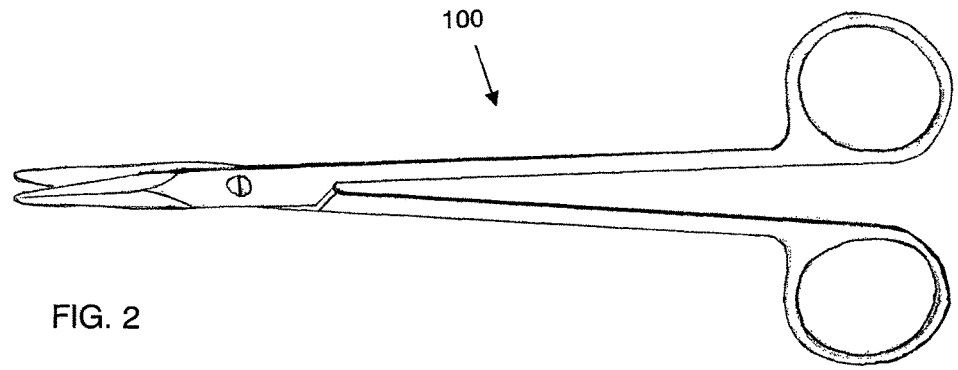
FIG. 2 is an illustration of an exemplary surgical instrument for protein contamination measurement, corresponding to the second image of the invention.

Next, the excitation light sources 22 are turned off and the visible light sources 20 are turned on. Whilst so illuminated, the camera 30 captures a second, visible image of the instrument 100 (see FIG. 2). As an example, with a white light source, 80 ms is an appropriate exposure time. It will be appreciated that this exposure time and that for the visible light source are merely exemplary and that the required exposure times will depend on a number of factors, including the stain, the lens 32, the camera 30 and the emission filter 34.

The non-reflective material covering the internal walls 16 of the chamber 14 doesn't fluoresce when illuminated by the excitation source 22.

It should be noted that the order of capturing the first and second images may be reversed, such that the 'second', visible image is in fact captured before the 'first', fluorescent image.

Figure 4:
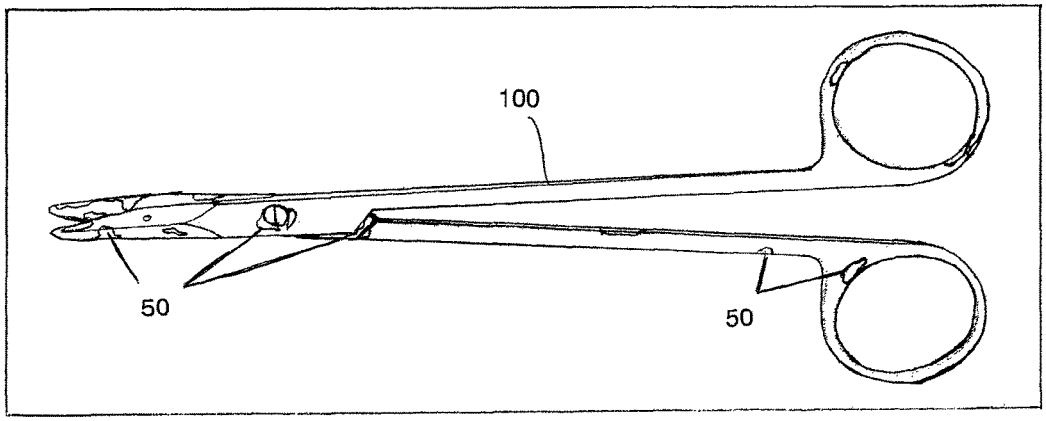
FIG. 4 is a composite image, comprising a combination of the images of FIGS. 2 and 3.

The camera 30 is connected to a processor (not shown) that is programmed with analysis and measurement software. The first and second images are overlaid and displayed by the software. In the combined image (see FIG. 4), the user can see areas of contamination 50 highlighted on the instrument 100. One method of overlaying the images would be to display the visible image in "red" and the fluorescent image in "green". This display gives the user a quick visual indication as to the presence or otherwise of protein residues on the instrument 100.

The analysis and measurement software of the system 10 can also analyse the fluorescent image to measure the total volume of stained protein 50 visible in the image. If the measured amount of stained protein 50 is greater than a pre-calibrated threshold, the system will flag the specimen 100 as being contaminated and unfit for use. One implementation would be to use a "traffic light" indicator, with "red" for contaminated and "green" for OK. An amber indicator might be used to indicate that the volume of protein is close to the threshold.

Measurements of the amount of stained protein 50 on the surgical instruments 100 under test are thus derived from the "fluorescent image". This first image should only contain signals corresponding to the emission from the stained protein. However it may contain some background signal level due to the camera 30 or imaging conditions.

To improve the accuracy of the measurements, the results may be corrected for any such extraneous signals. The measurement process thus consists of: summing the grey level values in the image; and background correcting the results to account for any background signal level or offset in the camera digitisation. Note that the background correction can be applied to the image data before measurement or to the results after measurement.

The background correction can be implemented in several ways. In a first embodiment, the first, fluorescent image is low pass filtered to produce a background image which is then subtracted from the original first image. In a second embodiment, the minimum signal level in the first, fluorescent image is measured and this minimum signal is then subtracted from the signal value at every point in the original first image. In a third embodiment, a background first image is captured without a specimen 100 inside the chamber 14 but with the excitation lights 22 turned on. This image would be subtracted on a pixel-by-pixel basis from each subsequent specimen image.

The measurement process may be fully automated, being initiated by a user once the specimen 100 has been loaded in to the chamber 14 and continuing until the measurement steps have all been completed. Alternatively, the system may be semi-automated, requiring user input at certain stages. It is also possible for the system to be fully manual, the user initiating each of the series of required steps in turn.

Improved accuracy might be achieved by repeating any or all of the image capture steps and the measurement and analysis steps. Also, the instrument 100 could be turned over after a first run so as to repeat the process on the reverse side.

In order to verify the accuracy of the system, it may be calibrated by testing a specimen having a known standard amount of protein contamination.

It will be appreciated that the specific locations and orientations of the light sources are exemplary and that alternative arrangements having no visible light source 20, just a single visible light source 20 or more than two visible light sources 20 are also possible. Likewise, there may be just a single excitation light source 22 or more than two excitation light sources 22. The excitation light sources 22 do not have to be located above respective visible light sources 20. The consideration is to provide as even illumination of the specimen 100 as possible.

Rather than a single camera 30 to capture both the first (fluorescing) image and the second (visible light) image, two separate cameras. Moreover, it will be understood that a digital camera 30 and associated lens 32 is just one example of an image capture device. Other devices capable of capturing the respective first and second images will be known to the skilled person. Furthermore, it will be understood that the image capture device(s) might be partially or fully located within the chamber 14.

The display of the first and second images and their combination is optional. It will be understood that for the purposes of determining whether a surgical instrument or other specimen is contaminated with protein it would be sufficient to provide a contamination indication, which might be visible or audible. At its most basic, the indication might be a light or an audible alert message that is turned on if patterns of fluorescence are detected in the first image.

The invention claimed is:

1. An imaging system for detection of protein contamination on a surgical instrument that has been treated with a fluorescing stain, wherein fluorophors in the stain are capable of emitting light of an emitted type when both excited by light of an excitation type and in contact with a protein, the system comprising:
    a chamber for receiving the surgical instrument;
    a first light source that emits light of the excitation type, arranged to illuminate the surgical instrument with light of the excitation type when, in use, the surgical instrument is received in the chamber;
    a first image capture device that captures a first image, of patterns of fluorescence emitted by the fluorophors in the stain on the surgical instrument, corresponding to protein contamination, when illuminated by the first light source;
    a second light source that emits visible light, arranged to illuminate the surgical instrument with visible light when, in use, the surgical instrument is received in the chamber;
    a second image capture device that captures a second image, of the surgical instrument, when illuminated by the second light source,
    masking means for rejecting all signals emanating from an area of the first image outside the outer boundary of the surgical instrument, the outer boundary of the surgical instrument being determined from the second image; and
    means for indicating, dependent on the first and second images and on the masking means, whether the surgical instrument is contaminated with protein.

2. The system of claim 1, further comprising means for determining the level of protein contamination.

3. The system of claim 2, wherein the means for determining the level of protein contamination comprises a processor and associated analysis software.

4. The system of claim 1, further comprising means to detect extraneous signals and means to compensate for any such signals.

5. The system of claim 1, further comprising a filter between the surgical instrument and the first image capture device, the filter transmitting light of the emitted type and preventing transmission of light of the excitation type.

6. The system of claim 5, wherein the filter transmits only light having a wavelength in the range of 430 nm to 450 nm.

7. The system of claim 1, wherein the light of the excitation type has a wavelength in the range of 270 nm to 370 nm.

8. The system of claim 7, wherein the light of the excitation type has a 312 nm peak wavelength.

9. The system of claim 1, further comprising an image combiner adapted to combine the first and second images.

10. The system of claim 1, wherein the first image capture device comprises a digital camera.

11. The system of claim 1, wherein the second image capture device comprises a digital camera.

12. The system of claim 11, wherein a single digital camera functions as both the first image capture device and the second image capture device.

13. The system of claim 2, wherein said means for indicating comprises an indicator adapted to indicate whether the level of protein contamination is below or above a predetermined threshold.

14. The system of claim 1, wherein the stain comprises a protein and/or amino acid detecting composition comprising:
    (a) o-phthaldialdehyde,
    (b) a C3-C6 thiol,
    (c) a buffer in the range of pH from 7.5 to 10, and
    (d) a surfactant,
    wherein the composition further comprises (e) a thiol reducing compound.

15. An imaging system for detection of protein contamination on a surgical instrument that has been treated with a fluorescing stain, wherein fluorophors in the stain are capable of emitting light of an emitted type when both excited by light of an excitation type and in contact with a protein, the system comprising:
    a chamber for receiving the surgical instrument;
    a first light source that emits light of the excitation type, arranged to illuminate the surgical instrument with light of the excitation type when, in use, the surgical instrument is received in the chamber;
    a first image capture device that captures a first image, of patterns of fluorescence emitted by the fluorophors in the stain on the surgical instrument, corresponding to protein contamination, when illuminated by the first light source;
    a second light source that emits visible light, arranged to illuminate the surgical instrument with visible light when, in use, the surgical instrument is received in the chamber;
    a second image capture device that captures a second image, of the surgical instrument, when illuminated by the second light source,
    a processor configured to determine an outer boundary of a surgical instrument from the second image, and then to reject all signals emanating from an area of the first image outside the outer boundary of the surgical instrument; and
    the processor being configured to analyze an area of the first image inside the outer boundary of the surgical instrument and output a signal indicating whether the surgical instrument is contaminated with protein.

* * * * *

UNITED STATES PATENT AND TRADEMARK OFFICE
CERTIFICATE OF CORRECTION

PATENT NO. : 9,664,686 B2
APPLICATION NO. : 13/817911
DATED : May 30, 2017
INVENTOR(S) : David Perrett et al.

Page 1 of 1

It is certified that error appears in the above-identified patent and that said Letters Patent is hereby corrected as shown below:

On the Title Page

Insert:
--(30) Foreign Application Priority Data
August 20, 2010 (UK)......................1014016.8--

Signed and Sealed this
Eighth Day of August, 2017

Joseph Matal
*Performing the Functions and Duties of the*
*Under Secretary of Commerce for Intellectual Property and*
*Director of the United States Patent and Trademark Office*